United States Patent [19]

Miyake et al.

[11] 4,255,607
[45] Mar. 10, 1981

[54] SEPARATION OF C$_8$ AROMATIC ISOMERS

[75] Inventors: Tetsuya Miyake; Kohji Inada; Motohisa Asano, all of Kawasaki, Japan

[73] Assignee: Asahi Kasei Kogyo Kabushiki Kaisha, Japan

[21] Appl. No.: 69,420

[22] Filed: Aug. 24, 1979

[30] Foreign Application Priority Data

Sep. 7, 1978 [JP] Japan .............................. 53-109118
Sep. 7, 1978 [JP] Japan .............................. 53-109119

[51] Int. Cl.³ .............................................. C07C 7/13
[52] U.S. Cl. .................................. 585/805; 585/825
[58] Field of Search ............................ 585/805, 825

[56] References Cited

U.S. PATENT DOCUMENTS

| 3,337,529 | 8/1967 | Laufer | 585/825 |
| 3,707,550 | 12/1972 | Stine et al. | 585/805 |
| 3,903,187 | 9/1975 | Geissler | 585/825 |

*Primary Examiner*—Herbert Levine
*Attorney, Agent, or Firm*—Sprung, Felfe, Horn, Lynch & Kramer

[57] ABSTRACT

A process for the adsorption separation of C$_8$ aromatic isomers which comprises the steps of:

(a) Supplying a C$_8$ aromatic isomer mixture to a separation zone packed with a zeolite adsorbent to form an C$_8$ aromatic isomer mixture adsorption band, the zeolite being a faujasite structured zeolite where at least about 60% of the exchangeable cation sites are replaced by potassium ion, and the remaining exchangeable cation sites being replaced by at least one metal cation selected from the group consisting of sodium, lithium, rubidium, cesium, magnesium, calcium, strontium, barium, nickel, copper, silver, manganese, cadmium, thallium and lanthanum ions;

(b) Supplying a desorbent to the separation zone to develop the C$_8$ aromatic isomer mixture adsorption band, the desorbent being an ether compound having a selectivity of about 0.3 to about 3.0 over para-xylene measured at a concentration of about 10 to about 90% by weight of the ether compound in the mixture of the ether compound and para-xylene;

(c) Repeating the step (a) and the step (b) alternately to effect the migration of the C$_8$ isomer mixture adsorption band; and (d) Collecting the entire amount of the C$_8$ aromatic isomer in fractions at the outlet of the separation zone.

22 Claims, 8 Drawing Figures

FIG.I-(1)
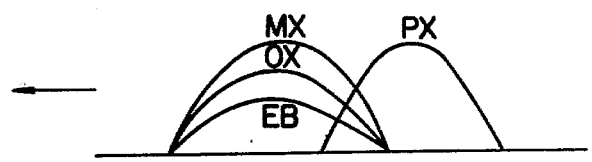
FIG.I-(2)
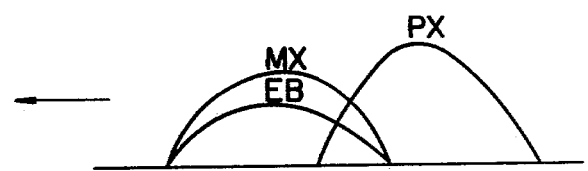
FIG.I-(3)
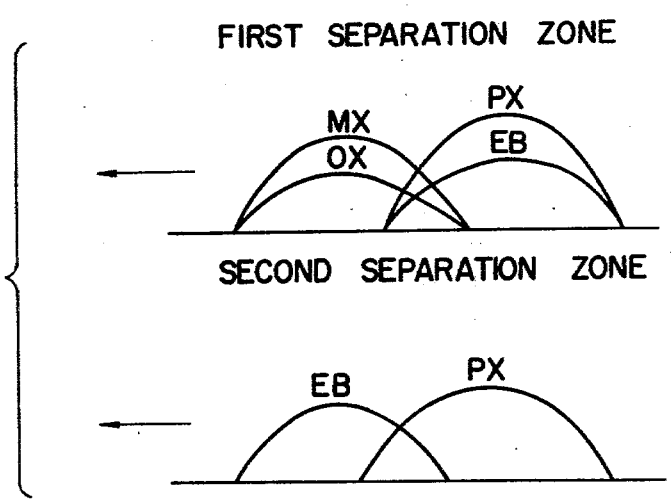

FIG.2-(1)
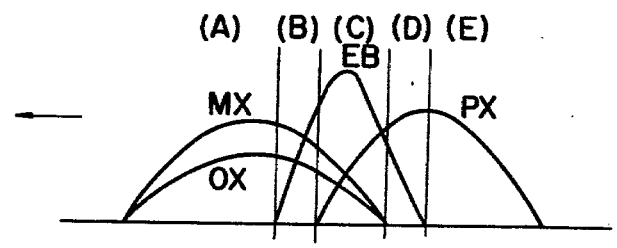
FIG.2-(2)
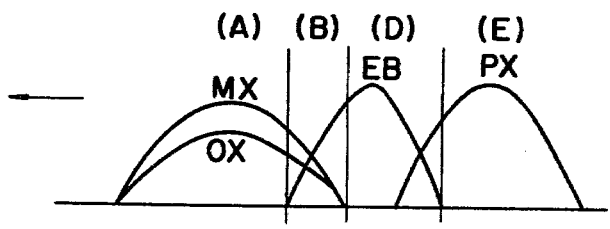
FIG.2-(3)
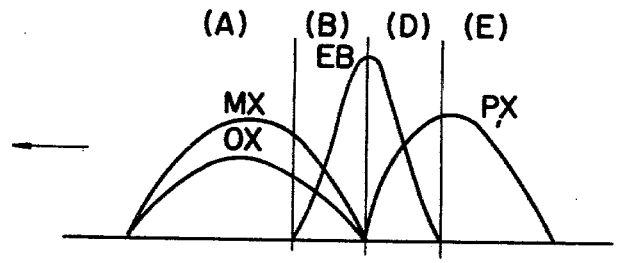

SEPARATION OF C₈ AROMATIC ISOMERS

BACKGROUND OF THE INVENTION

1. Field of the Invention

This invention relates to a process for the selective adsorption separation of mixed aromatic hydrocarbon isomers having 8 carbon atoms (hereinafter "C$_8$ aromatic isomers") by a zeolite adsorbent.

For simplicity in the following explanation, para-xylene, ortho-xylene, meta-xylene, ethylbenzene and a desorbent are denoted by the symbols "PX", "OX", "MX", "EB" and "DS", respectively.

Also, the selectivity of a system comprising a zeolite adsorbent and a solution for one substance A over another substance B is denoted by the formula;

$$K_A{}^B = \frac{X_B}{Y_B} \bigg/ \frac{X_A}{Y_A}$$

wherein $X_A$ represents a concentration of substance A in the zeolite adsorbent phase; $X_B$ represents a concentration of substance B in the zeolite adsorbent phase; $Y_A$ represents a concentration of substance A in the external solution adjacent to the zeolite adsorbent; and $Y_B$ represents a concentration of substance B in the external solution adjacent to the zeolite adsorbent.

For example, $K_{MX}{}^{PX}$ denotes a selectivity of a zeolite adsorbent for para-xylene over meta-xylene and $K_{PX}{}^{DS}$ denotes a selectivity of a zeolite adsorbent for a desorbent over para-xylene.

2. Description of the Prior Art

C$_8$ aromatic isomers are supplied from, for example, naphtha-crackers, reformers or disproportionation process of toluene. Conventionally C$_8$ aromatic isomers are separated by distillation, crystallization, extraction of HF-BF$_3$ complex of MX or selective adsorption by a zeolite adsorbent. Also, separation of C$_8$ aromatic isomers is conducted on an industrial scale with an isomerization process which is to convert, MX, OX, and EB into PX. Of many industrial separation processes the selective adsorption process by a zeolite adsorbent is generally considered the most economical process.

In conducting the selective adsorption of C$_8$ aromatic isomers by a zeolite adsorbent the important points are firstly to select a zeolite adsorbent having a high selectivity for one C$_8$ aromatic isomer over another C$_8$ aromatic isomer and secondly to select a most appropriate desorbent for the separation process employed.

It is known that aromatic hydrocarbons such as toluene, benzene, diethylbenzene and cumene; naphthalenes; alcohols; and ketones can be used as desorbents in the adsorption separation of C$_8$ aromatic isomers.

In conducting the adsorption separation process there are two types of separation systems. One is a so-called "displacement chromatography" and the other a so-called "elution chromatography". According to the so-called "displacement chromatography", an C$_8$ aromatic isomer adsorption band migrates while a frontal and a rear desorbents are kept adjacent to both frontal and rear boundaries of the C$_8$ aromatic isomer adsorption band, respectively, and the C$_8$ aromatic isomer adsorption band and the desorbent adsorption band are kept separated from each other. According to this type of operation, the boundaries between the C$_8$ aromatic isomer adsorption band and the desorbent do not diffuse and, therefore, advantageously products can be obtained at a high concentration of C$_8$ aromatic isomers. However, there is required a regeneration operation of displacing the rear desorbent by the frontal desorbent after the development of the C$_8$ aromatic isomer adsorption band and thus a large amount of heat consumption is indispensable for heating or washing with a large amount of the frontal desorbent.

On the other hand, according to the so-called "elution chromatography", a desorbent enters the C$_8$ aromatic isomer adsorption band and accordingly, when the selectivity for one C$_8$ aromatic isomer over another C$_8$ aromatic isomer is low and a considerably long migration distance of the C$_8$ aromatic isomer adsorption band is necessary for achieving a desired degree of separation, the C$_8$ aromatic isomer adsorption band is diluted with a large amount of the desorbent, resulting in a large heat consumption.

According to many of the conventionally proposed adsorption separation processes by a zeolite adsorbent, PX is, in general, recovered as a product. One separation process comprises adsorbing PX alone as an adsorptive component on a zeolite adsorbent in an adsorption separation zone to recover PX as a product and passing OX, MX and EB as non-adsorptive components into an isomerization reaction. Another separation process comprises adsorbing PX alone on a zeolite adsorbent in an adsorption separation zone to recover PX as a product and passing OX and MX into an isomerization reaction zone after removal of EB from OX, MX and EB by super rectification. A further separation process as described in Japanese Patent Publication Nos. 29300/1977 and 29730/1977 comprises passing a feed mixture and an isomerization effluent to an OX separation zone to separate OX by distillation, selectively retaining PX and Eb as adsorptive components on a zeolite adsorbent in a first adsorption separation zone, passing MX as a non-retained component into an isomerization reaction zone while selectively retaining PX or EB on a zeolite adsorbent of a second adsorption separation zone to separate PX and EB. In the first and the second processes of the above described three methods, the selectivities which determine the ease in separating OX, MX and EB as non-absorptive components from PX as an adsorptive component are $K_{EB}{}^{PX}$ and $K_{MX(OX)}{}^{PX}$ and the degree of separation is determined by the lowest value among these selectivities. In the third process as described above, the selectivity which determines the degree of separation in the first adsorption separation zone is $K_{MX}{}^{EB}$ and $K_{MX}{}^{PX}$ and the selectivity which determines the degree of separation in the second adsorption separation zone is $K_{EB}{}^{PX}$. According these conventional processes, there are such restrictions that the separation operation must be conducted by a zeolite adsorbent whose $K_{MX(OX)}{}^{PX}$ is nearly equal to the low $K_{EB}{}^{PX}$ and under the conditions where $K_{MX}{}^{PX}$ is nearly equal to the low $K_{EB}{}^{PX}$ and $K_{MX(OX)}{}^{EB}$. In order to obtain a desired degree of separation in conducting the adsorption separation with a low selectivity, a long migration distance of an C$_8$ aromatic isomer adsorption zone is required, and the C$_8$ aromatic isomer adsorption zone is diluted with a large amount of a desorbent and the process operation becomes a so-called "elution chromatography". The desorbent used in this conventional process can be selected within a wide range of desorbents but from the economical viewpoint the process is not advantageous.

SUMMARY OF THE INVENTION

An object of this invention is to provide a desorbent which does not reduce the selectivity and adsorption capacity of a zeolite adsorbent, which has a suitable desorbing power which is not reduced at the boundaries of a band where the xylene concentration is low and which can easily recovered from $C_8$ aromatic isomers by distillation.

Another object of this invention is to provide a process for the adsorption separation of $C_8$ aromatic isomers by effectively using the desorbent as described above.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

Accordingly, the present invention in one embodiment provides a process for the adsorption separation of $C_8$ aromatic isomers which comprises the steps of:

(a) Supplying a $C_8$ aromatic isomer mixture to a separation zone packed with a zeolite adsorbent to form an $C_8$ aromatic isomer mixture adsorption band, said zeolite being a faujasite structured zeolite where at least about 60% of the exchangeable cation sites are replaced by potassium ion, and the remaining exchangeable cation sites being replaced by at least one metal cation selected from the group consisting of sodium, lithium, rubidium, cesium, magnesium, calcium, strontium, barium, nickel, copper, silver, manganese, cadmium, thallium and lanthanum ions;

(b) Supplying a desorbent to the separation zone to develop the $C_8$ aromatic isomer mixture adsorption band, said desorbent (DS) being an ether compound having a selectivity ($K_{PX}^{DS}$) of about 0.3 to about 3.0 over PX measured at a concentration of about 10 to about 90% by weight of the ether compound in the mixture of the ether compound and PX;

(c) Repeating the step (a) and the step (b) alternately to effect the migration of the $C_8$ isomer mixture adsorption band; and (d) Collecting the entire amount of the $C_8$ aromatic isomers in fractions at the outlet of the separation zone.

The present invention in another embodiment provides a process for the adsorption separation of $C_8$ aromatic isomers which comprises the steps of:

(a) Supplying a $C_8$ aromatic isomer mixture containing at least one of OX and MX, and in addition, EB and PX to a first separation zone packed with a zeolite adsorbent to form a $C_8$ aromatic isomer mixture adsorption band;

(b) Supplying the desorbent as described above to the separation zone to develop the $C_8$ aromatic isomer mixture adsorption band where the following regions (A), (B), (C), (D) and (E) in the order to the direction of migration are formed, Region (A) containing OX and/or MX,
Region (B) containing OX and/or MX and EB,
Region (C) containing OX and/or MX, EB and PX, the region (C) being missing if the regions (A) and (B) contain the total amount of OX and MX and the regions (D) and (E) contain the total amount of PX,
Region (D) containing EB and PX, and
Region (E) containing PX;

(c) Repeating the step (a) and the step (b) alternately to effect the migration of the $C_8$ aromatic isomer mixture adsorption band; and (d) Collecting the entire amount of the regions (A), (B), (C), (D) and (E) in fractions at the outlet of the separation zone.

BRIEF DESCRIPTION OF THE DRAWINGS

FIG. 1 (1), (2) and (3) illustrate the typical examples of the conventionally employed adsorption separation patterns.

FIG. 2 (1), (2) and (3) illustrate the adsorption separation patterns which can be employed in the separation process of this invention.

DETAILED DESCRIPTION OF THE INVENTION

Figure 3:
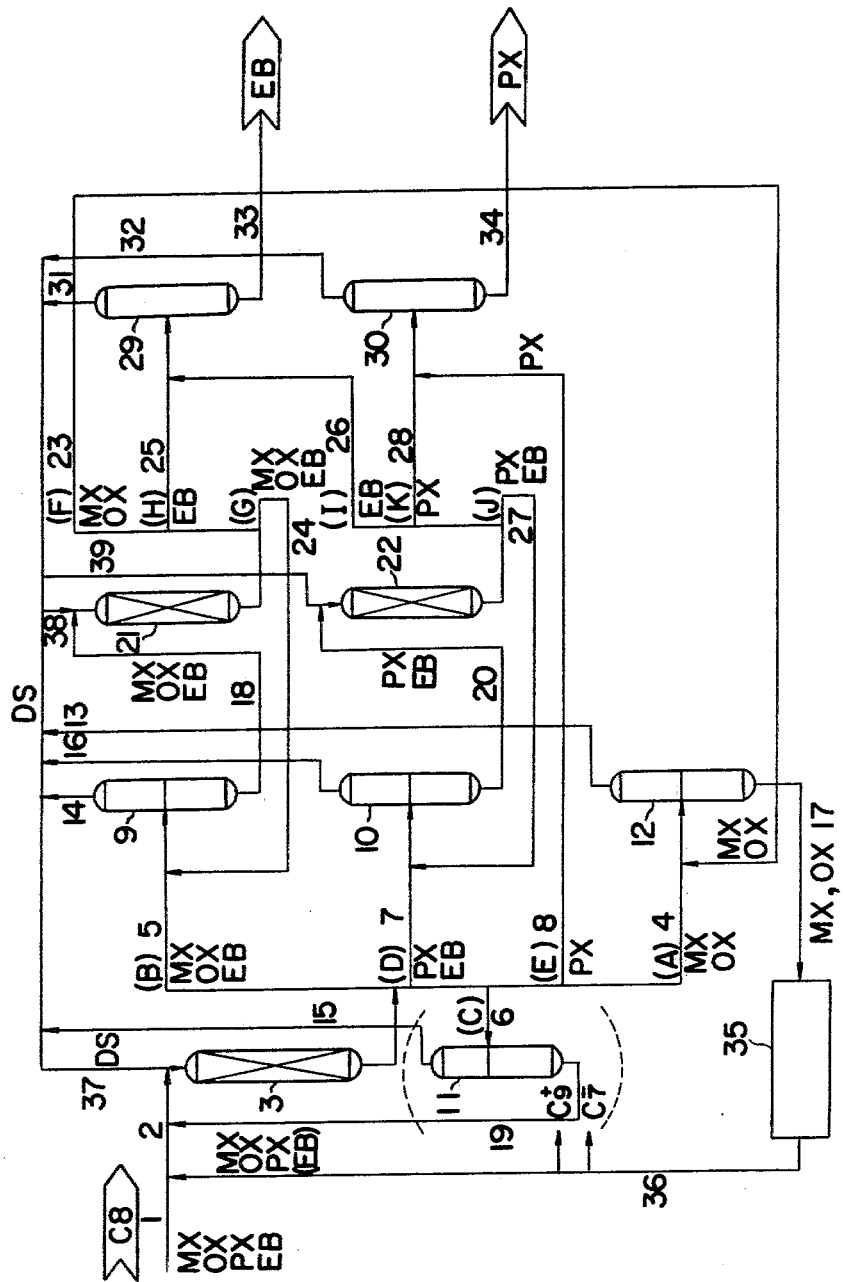
FIG. 3 illustrates the flow diagram of a separation system of one embodiment of this invention.

It is necessary that the zeolite adsorbent which can be employed in this invention has a high selectivity for one xylene isomer over another xylene isomer. It is preferred that especially $K_{MX(OX)}^{PX}$ is at least about 4. In order to increase $K_{MX(OX)}^{PX}$, (i) the type of zeolite, (ii) the exchanged metal ion and (iii) the condition of activation are required to be optimized.

The zeolites which can be preferably employed in this invention are crystalline aluminosilicates having a 6-ring structure and a poly-hedral cage of $\beta$,26-hedron including natural faugasites and synthetic zeolite type X and zeolite type Y. Of these zeolites, a synthetic zeolite type Y having a high $SiO_2$ to $Al_2O_3$ ratio and a high $K_{MX}^{PX}$ is preferred. A synthetic zeolite type Y having a $SiO_2$ to $Al_2O_3$ mole ratio of at least about 4.0 is more preferred. The zeolites as disclosed in the copending application Ser. Nol 3453, filed on Jan. 15, 1979, titled "IMPROVED ZEOLITE ADSORBENT AND METHOD OF PREPARATION SAME" are particularly preferred in the present invention. Thus, the subjecting matter of said copending application is herein incorporated by reference.

The type of metal cations located the exchangeable cation sites of the zeolite relates to the selectivities such as $K_{MX}^{PX}$. In this invention it is preferred that the exchangeable cation sites of the zeolites are replaced with potassium ion as one component and at least one metal cation selected from sodium, lithium, rubidium, cesium, magnesium, calcium, strontium, barium, nickel, copper, silver, manganese, cadmium, thallium and lanthanum ions as the other component. Further, it is more preferred that at least about 60% of the exchangeable cation sites are replaced with potassium ion and the remaining are replaced with at least one cation selected from lithium, barium, thallium and cesium ions.

Preferably the zeolites have been subjected to a calcination at a temperature typically ranging from about 100° C. up to a temperature below the decomposition temperature of the faujasite structure, preferably from about 150° C. to about 600° C. and more preferably from about 300° C. to about 500° C. and preferably for about 3 hours to 72 hours.

The zeolites of this invention has also considerably high $K_{EB}^{PX}$ and $K_{MX}^{EB}$ and can be satisfactorily used in a second and a third separation zones.

With most of the desorbents which are generally considered appropriate for the adsorption separation of $C_8$ aromatic isomers, their $K_{PX}^{DS}$ shows the depending on the concentration of the desorbent present and tends to decrease at high concentrations of the desorbent. Such desorbents have a desorbing power at the center part of the elution curve of the $C_8$ aromatic isomer adsorption based where $K_{PX}^{DS}$ is appropriate but at the rear end of the $C_8$ aromatic isomer adsorption band where the concentration of the $C_8$ aromatic isomers is low, $K_{PX}^{DS}$ decreases and the desorbents tend to loose the desorbing power. Consequently the elution curve brings about the abnormal and long tailing and the concentration of the $C_8$ aromatic isomers is remarkably reduced.

Furthermore, it is preferred that a desorbent, as another requisite, does not reduce a selectivity for one $C_8$ aromatic isomer over another $C_8$ aromatic isomer ($K_A^B$) but rather the desorbent increases $K_A^B$ in the $C_8$ aromatic isomer adsorption band which the desorbent enters. A desorbent of a strong adsorbability having a high $K_{PX}^{DS}$ often disadvantageously reduces $K_A^B$ and the adsorption capacity of $C_8$ aromatic isomers due to the large amount of the desorbent adsorbing on the zeolite adsorbent. On the other hand, a desorbent of a weak adsorbability having a low $K_{PX}^{DS}$ cannot effect a sufficient migration of the $C_8$ aromatic isomer adsorption band and as a result, the $C_8$ aromatic isomers are left behind and the separation of $C_8$ aromatic isomers becomes impossible.

In this sense, according to this invention $K_{PX}^{DS}$ ranges typically from about 0.3 to about 3.0 and preferably from about 0.5 to about 1.5 in a wide range of the concentration of desorbent.

When an average concentration of $C_8$ aromatic isomers in the $C_8$ aromatic isomer adsorption band at the time of collecting products separated is comparatively high and at least 20% and the frontal and the rear boundaries of the $C_8$ aromatic isomer adsorption band are sufficiently sharp, the above described desorbent is most effectively used. This band shape can be realized by using an adsorbent having a comparatively high $K_A^B$ and by finishing separation within a comparatively short migration distance, i.e., when the maximum concentration of $C_8$ aromatic isomers in the single adsorption bnad, and the frontal and the rear boundaries of the $C_8$ aromatic isomer adsorption band are comparatively sharp.

The desorbent which can be employed in this invention is an ether compound having a selectively ($K_{PX}^{DS}$) of about 0.3 to about 3.0 measured at a concentration of about 10 to about 90% by weight of the ether compound in the mixture of the ether compound and PX. Preferred ether compounds have a $K_{PX}^{DS}$ of about 0.5 to about 1.5.

Specific examples of suitable ether compounds include diisopropyl ether, diisobutyl ether, di-sec-butyl ether, di-tert-butyl ether, di-n-amyl ether, diisoamyl ether, di-tert-amyl ether, furan, 2-methylfuran, hexamethylene oxide, 1,4-cineole and 1,8-cineole. Of these ether compounds, diisopropyl ether, diisobutyl ether and 1,8-cineole are preferred. A more preferred ether compound is diisopropyl ether since the adsorption/desorption characteristics do hardly depend upon the concentration of the desorbent, the boiling point is considerably remote from those of xylene isomers and the volitility is high.

The characteristic feature of the present process is to employ specific adsorption separation patterns as illustrated in FIG. 2(1), (2) and (3) which differ from the conventionally employed ones as illustrated in FIG. 1(1), (2) and (3) by increasing $K_{MX(OX)}^{PX}$ as much as possible in a first separation zone packed with a zeolite adsorbent to which a $C_8$ aromatic isomer mixture containing at least one of OX and MX, and in addition EB and PX is supplied. According to the specific adsorption separation patterns which can be employed in this invention, the adsorption peak of EB region appears between the adsorption peak of MX or OX region and the adsorption peak of PX region in the $C_8$ aromatic isomer mixture adsorption band. In order to more efficiently conduct the separation of $C_8$ aromatic isomers under the conditions of a high $K_{MX(OX)}^{PX}$ while maintaining these adsorption separation patterns, it is preferred to employ, as desorbents, the ether compounds as described above.

A preferred separation system will now be explained.

In collecting each of regions (A), (B), (C), (D) and (E), when a considerable amount of region (C) containing every feed component is present due to the low degree of separation as illustrated in FIG. 2(1), the $C_8$ aromatic isomer mixture collected from region (C) is preferably recycled to and combined with a fresh feed for separation zone. The OX and/or MX as such collected from region (A) can be recovered, if desired, as a product but at least part of the OX and/or MX is preferably passed into an isomerization zone to convert at least part thereof into EB and/or PX, and the effluent containing the EB and/or PX converted in the isomerization zone is recycled to and combined with the fresh feed for separation zone. The mixture collected from region (B) can be subjected to the selective adsorption separation in a third separation zone packed with a zeolite adsorbent to obtain EB as a product, and the MX and/or OX separated in the third separation zone are combined with the $C_8$ aromatic isomer mixture collected from region (A) and then passed into the isomerization zone as described above. Also, the $C_8$ aromatic isomer mixture collected from region (B) can be directly passed into the isomerization zone together with the $C_8$ aromatic isomer mixture collected from region (A). The $C_8$ aromatic isomer mixture containing EB and PX collected from region (D) can be subjected to the selective adsorption separation in a second separation zone packed with a zeolite adsorbent to obtain EB and PX as a product, respectively, at the same time.

The adsorption separation patterns in the third separation zone or in the second zone again, respectively, are different from those in the first separation zone due to, firstly, the separation of two $C_8$ aromatic isomers and, secondly, the lower $K_{EB}^{PX}$ and $K_{MX(OX)}^{EB}$ compared with $K_{MX}^{PX}$. However, there can preferably employed the same chromatographic separation process as in the first separation which comprises (a) supplying the $C_8$ aromatic isomer mixture to a third or a second separation zone packed with a zeolite adsorbent to form an $C_8$ aromatic isomer mixture adsorption band; (b) supplying a desorbent on the third or the second separation zone to develop the $C_8$ aromatic isomer mixture adsorption band; (c) repeating the step (a) and the step (b) as described above alternately to effect the migration of the $C_8$ aromatic isomer mixture adsorption band; and (d) collecting the entire amount of the $C_8$ aromatic isomers in fractions at the outlet of the third or the second separation zone. It is more preferred that the same ether compound as in the first separation zone is employed as a desorbent in the third or the second separation zone.

As a combination of the separation processes which can be employed in this invention, there can preferably employed a closed system of passing non-adsorptive components MX and OX alone or together with EB in the region of MX and OX into an isomerization zone to convert at least part of MX and OX into PX and/or EB and recycling the effluent containing the PX and/or EB converted from the isomerization zone to the first separation zone.

The isomerization reaction of this invention can be conducted by any conventionally known method. For example, the isomerization of $C_8$ aromatic isomers can be effected by passing the $C_8$ aromatic isomer feed to the packed catalyst layer containing, as its main component, silica-alumina or a noble metal and/or a non-noble metal supported on a silica-alumina.

To provide a clearer and better understanding of this invention, reference will now be made to preferred embodiments thereof illustrated in FIG. 3 and FIG. 4.

Figure 4:
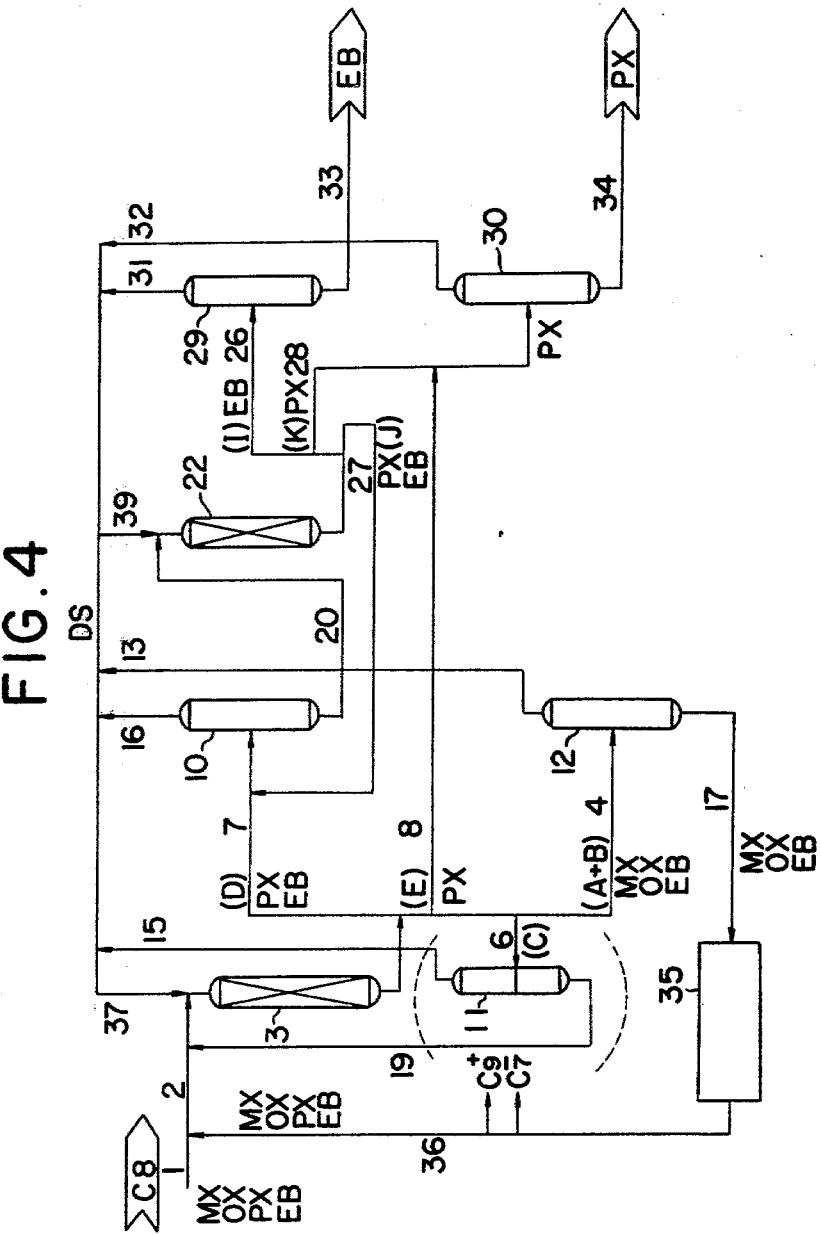
FIG. 4 illustrates the flow diagram of a separation system of another embodiment of this invention.

In the embodiment illustrated in FIG. 3 the $C_8$ aromatic isomers alone collected from the above described region (A) are passed into an isomerization zone, and in another embodiment illustrated in FIG. 4 the $C_8$ aromatic isomers collected from the above described regions (A) and (B) are passed into an isomerization zone.

In FIG. 3 and FIG. 4 a first separation zone 3, a second separation zone 22 and a third separation zone 21 are adsorption separation zones packed with a zeolite adsorbent, respectively, and at the inlet of the separation zones is supplied a $C_8$ aromatic isomer mixture and at the outlet of the separation zones can be collected each component of the $C_8$ aromatic isomer mixture in fractions. In an isomerization zone 35 part of OX and MX or OX, MX and EB can be converted into PX and/or EB.

In FIG. 3 a fresh feed containing four major $C_8$ aromatic isomers, i.e., MX, OX, PX and EB through line 1 is combined with an effluent from isomerization zone 35 through line 36 and fraction (C) containing the four major $C_8$ aromatic isomers which is separated as an intermediate region in first separation zone 3 and passed through line 6 into separation means 11 where the desorbent is removed, and the feed thus combined is supplied to first separation zone 3 through line 2 to form a $C_8$ aromatic isomer mixture adsorption band. Then the desorbent recovered from separation means 9, 10, 11, 12, 29 and 30 through lines 14, 16, 15, 13, 31 and 32 respectively, is supplied to first separation zone 3 to develop the $C_8$ aromatic isomer mixture adsorption band, and by alternately repeating the supply of the $C_8$ feed containing MX, OX, PX and EB and that of the desorbent to separation zone 3, the $C_8$ aromatic isomer mixture adsorption band migrates to the outlet of separation zone 3, and the entire amount of the $C_8$ aromatic isomers is collected in fractions (A), (B), (C), (D) and (E).

Firstly, fraction (A) containing MX and OX and additionally a quantity of desorbent is passed through line 4 into separation means 12 where MX and OX is separated from the desorbent which is returned to each separation zone 3, 21 or 22. The MX and OX separated is passed into isomerization zone 35 through 17.

Secondly, fraction (B) containing MX, OX and EB and additionally a quantity of desorbent is passed through line 5 into separation means 9 where MX, OX and EB is separated from the desorbent, and the MX, OX and EB recovered is passed through line 18 into third separation zone 21 to separate three $C_8$ aromatic isomer fractions (F), (H) and (G) by supplying the desorbent through line 38 for developing the $C_8$ aromatic isomer adsorption band, and by alternately repeating the supply of the three $C_8$ aromatic isomers and that of the desorbent into third separation zone 21, separation of EB from MX and OX are continuously effected. Fraction (F) contains a mixture of MX and OX, fraction (H) EB only and fraction (G) MX, OX and EB, and each fraction contains, in addition, the same desorbent.

Thirdly, fraction (C) containing MX, OX, PX and EB and additionally a quantity of desorbent is passed through 6 into separation means 11 where the four $C_8$ aromatic isomers are separated from the desorbent, and the four $C_8$ aromatic isomers separated are combined with the fresh feed through line 19.

Fourthly, fraction (D) containing PX and EB and additionally a quantity of desorbent is passed through line 7 into separation means 10 where PX and EB are separated from the desorbent and the PX and EB recovered are supplied through line 20 to second separation zone 22 to separate three $C_8$ aromatic isomer fractions (I), (J) and (K) by supplying the desorbent through line 39 developing the $C_8$ aromatic isomer adsorption band, and by alternately repeating the supply of the $C_8$ aromatic isomers and that of the adsorbent to second separation zone 22, the separation of PX and EB is continuously conducted. Fraction (I) contains EB and a quantity of desorbent, fraction (J) contains PX, EB and a quantity of desorbent and fraction (K) contains PX and a desorbent.

Fifthly, fraction (E) containing PX and a quantity of desorbent is combined through line 8 with fraction (K) as described above through line 28, and then passed into separation means 30 where PX is separated from the desorbent, resulting in the recovery of PX as a product through line 34.

Further, fraction (F) containing MX, OX and a quantity of desorbent is passed via line 23 into separation means 12 together with fraction (A) as above described and then via line 17 into isomerization zone 35 after removal of the desorbent. Fraction (G) containing MX, OX, EB and a quantity of desorbent is recycled via line 24 to separation means 9 together with fraction (B) as above described. Fraction (H) containing EB and a quantity of desorbent is combined via line 25 with fraction (I) as described above via line 26, and then passed into separation means 29 where EB is separated from the desorbent, resulting in the recovery of the EB as a product through line 33. Fraction (J) containing PX, EB and a quantity of desorbent is recycled via line 27 to separation means 10 together with fraction (D) as described above via line 7.

The desorbent recovered is collected through lines 13, 14, 15, 16, 31 and 32, respectively, and supplied to separation means 3, 21 and 22 through lines 37, 38 and 39, respectively, for re-use as the desorbent.

In a further embodiment of this invention which is a modification of the separation system illustrated in FIG. 3 where fraction (C) collected at the outlet of separation zone 3 does not exist as illustrated in FIG. 2(3), desorbent separation means 11 and the effluent therefrom via line 15 or 19 are accordingly omitted from the separation system illustrated in FIG. 3.

In the embodiment of this invention illustrated in FIG. 4, fraction (A) and fraction (B) which are collected at the outlet of separation zone 3 in the separation system as illustrated in FIG. 3 are together passed into an isomerization zone. According to this process, the number of separation zones and desorbent separation means can be reduced by one, respectively, compared with the process as illustrated in FIG. 3 but the entire amount of EB cannot be recovered as a product.

More specifically, a fresh feed containing MX, OX, PX and EB via line 1, an effluent from isomerization zone 35 via line 36 and fraction (C) containing MX, OX, PX, EB and a quantity of desorbent which is separated in first separation zone 3 and passed via line 6 to separation means 11 where the desorbent is removed, via 19 are combined together and supplied to first separation zone 3 to form a $C_8$ aromatic isomer mixture adsorption band. Then the desorbent recovered from separation means 9, 10, 11, 12, 29 and 30 via lines 14, 16, 15, 13, 31 and 32, respectively is supplied via line 37 to separation zone 3 to develop the $C_8$ aromatic isomer mixture adsorption band, and by alternately repeating the supply of the feed containing MX, OX, PX and EB and that of the desorbent the $C_8$ aromatic isomer mixture adsorption band migrates and at the outlet of separation zone 3 the entire amount of the $C_8$ aromatic isomers is collected in fractions (A), (B), (C), (D) and (E). Of these fractions, fraction (A) and (B) together containing MX, OX and EB and additionally a quantity of desorbent are passed via line 4 into separation means 12 where the desorbent is removed, and then the MX, OX and EB separated are passed into isomerization zone 35 via line 17. Fraction (C) containing MX, OX, PX and EB and a quantity of desorbent is passed via line 6 into separation means 11 where the desorbent is removed, and then combined with a fresh feed via line 19. Fraction (D) containing PX, EB and a quantity of desorbent is passed into separation means 10 where the desorbent is removed, and then supplied to second separation zone 22 to separate three $C_8$ aromatic isomer fractions (I), (J) and (K) as in FIG. 4. Fraction (I) containing EB and a quantity of the desorbent is passed into separation means 29 where the desorbent is removed, resulting in the recovery of EB as a product through line 33. Fraction (J) containing PX, EB and a quantity of desorbent is combined through line 27 with fraction (D) through line 7 and passed into separation means 10 and supplied to second separation zone 22 after removal of the desorbent. Fraction (K) containing PX and a quantity of desorbent is combined through line 28 with fraction (E) through line 8 and passed into separation means 30 where PX is separated from the desorbent, resulting PX as a product through line 34.

When passing of region (A) alone to an isomerization zone as in FIG. 3 is compared with passing of region (A) and region (B) together to an isomerization zone as in FIG. 4, the former separation system consumes less heat due to the small feed amount, i.e., MX and OX alone are supplied to the isomerization zone. Further, since the feed does not contain EB, it is unnecessary to use a catalyst of an expensive noble metal on a support material. Moreover, the entire amount of EB in a feed $C_8$ aromatic isomer mixture and the entire amount of EB produced in the isomerization reaction can be advantageously recovered as a product but three separation zones and six desorbent separation means are required.

On the other hand, according to the latter separation system, the amount passed into the isomerization zone is increased a little due to the mixing of EB therein and as a result, the consumption of heat is increased. Further, a catalyst of a noble metal on support material is required as the isomerization catalyst and the amount of EB produced is decreased since part of EB is recycled to the first separation zone via the isomerization zone. However, the number of separation zones and desorbent separation means is advantageously reduced from three to two and from six to five, respectively.

In comparing these two separation systems from the economical viewpoint, the former is, in general, a little favorable because the desorbent separation zones annexed to the second and third means are of a relatively small size and without increasing the cost of construction, more EB can be obtained. In other points the selection of these system can be made depending on the environmental factors such as the demand for EB.

In a still further embodiment of this invention which is a modification of the separation system illustrated in FIG. 4 where fraction (C) collected at the outlet of separation zone 3 does not exist as in FIG. 2(3), desorbent separation means 11 and the effluent therefrom via line 15 or 19 can be accordingly omitted from the separation system illustrated in FIG. 4.

The desorbent which can be used in the first, second and third separation zones may be the same or different. With respect to the same desorbent used in the first, second and third separation zones, when the desorbent is removed in a desorbent separation means, a considerably high amount of the desorbent can be permitted to mix with the $C_8$ aromatic isomer mixture which is supplied to the subsequent separation zone and also there is no trouble about deterioration of a zeolite adsorbent packed in the second or third separation zone or other disadvantages which can be caused by desorbent which differs from that used in the first separation zone. Further, it is preferred from the economical and operational viewpoints to use the same desorbent in the first, second and third separation zones. For example, when the desorbent separation means is a distillation column, even several percentages of the desorbent which are mixed with an effluent of the $C_8$ aromatic isomers from the top or the bottom of the distillation column have hardly any influence over the second or third separation zone and the cost of distillation can be reduced.

The velocity of development of a $C_8$ aromatic isomer adsorption band and the flow rate of a desorbent can be arbitrarily determined. In the process of a comparatively high $K_B^4$, a relatively high separation is accomplished before diffusion of the adsorption band and the amount of separation per unit time is increased by increasing the flow rate. However, remarkably increased flow rates cause a pressure drop of the adsorbent packed bed and are disadvantageous from the economical viewpoint. On the other hand, in the process of a relatively low $K_B^4$, a most preferred flow rate is suitably selected. In general, the linear flow rate in a vacant separation column ranges from about 0.5 m per hour to about 80 m per hour.

Higher temperatures of development operation are preferred from the standpoint of the rate of adsorption and desorption while comparatively low temperatures are preferred from the standpoint of adsorption capacity. In general, the temperature of development of this invention ranges from about 20° C. to about 200° C. A preferred temperature ranges from about 40° C. to about 160° C. When the development is conducted using a desorbent having a low boiling point at a temperature above its boiling point, it is necessary to feed the $C_8$ aromatic isomer mixture above the total pressure of the vapor pressure of the desorbent and the pressure drop of the adsorbent packed.

The separation zone which can be employed in this invention may be any vessel capable of forming a fixed bed packed with a zeolite adsorbent therein, and as such a vessel, a cylindrical column having one inlet for liquid and one outlet for liquid at least at one location can be employed. It is preferred that the cylindrical column has a plate for uniformly distributing liquid and a plate for uniformly collecting liquid provided at the inlet and at the outlet of the column, respectively, in order to prevent the re-mixing of products separated due to the occurrence of mixing of liquids and whirlpool of liquid. When the diameter of an adsorbent-packed column and the length of the adsorbent-packed layer (column length) are large, the adsorption separation can be conducted using a plurality of columns in addition to one column. In this case, the outlet for liquid of one column is connected to the inlet for liquid of another column through a conduit and liquid is collected from the outlet of the last column.

Also it is preferred that the column equipments are provided with an on-off valve or a three-way valve for feeding a $C_8$ aromatic isomer mixture and a desorbent or a switch-over valve, e.g., a three-way, four-way or multi-way switch-over valve for collecting products separated in fractions. Furthermore, a detector for detecting the concentration of the $C_8$ aromatic isomer mixture and/or the desorbent can be preferably provided with the conduit where liquid flows or the bottom of the column for operating the switch-over valves to regulate the supply of feedstock and the collection of products.

Major advantages of the adsorption separation by the specific ether compounds of this invention over the conventional adsorption separation are as follows:

1. The heat consumption required to distill the desorbent is greatly reduced, partly because of the high concentration of $C_8$ aromatic isomers separated.

2. The amount of a zeolite adsorbent packed in the second and the third separation zone as well as in the first separation zone, the cost of recovering the desorbent and the cost of construction can be reduced, because the adsorption separation can be conducted under the operational condition of a maximum $K_{MX}^{PX}$.

3. Part of EB or all EB in the $C_8$ aromatic isomer mixture can be recovered as a product so that the production cost incurred to PX can be reduced. Also, the production amount of EB can be arbitrarily controlled.

The following Examples are given to illustrate the present invention more specifically. However, it should be understood that the invention is in no way limited to these specific embodiments. In these Examples all percentages are by weight unless otherwise indicated.

REFERENTIAL EXAMPLE

A commercially available synthetic faujasite structured zeolite type Y (Na type; mole ratio of $SiO_2/Al_2O_3 = 4.8$) was contacted with a potassium nitrate aqueous solution until at least 80 percent of the ion exchangeable sites located on the zeolite were replaced by potassium ion. Then the zeolite thus ion-exchanged was thoroughly washed with water and calcined at 400° C. for 2 hours.

With each of the desorbents as set forth in Table 2, liquids to be equilibriated to the zeolite adsorbent (hereinafter referred to equilibrium liquids) having the compositions as set forth in Table 1 were prepared by using n-decane as a diluent.

TABLE 1

|   | n-Decane (weight %) | p-Xylene (weight %) | Desorbent (weight %) | Desorbent/ p-Xylene + Desorbent (weight %) |
|---|---|---|---|---|
| 1 | 70 | 27 | 3 | 10 |
| 2 | 70 | 22.5 | 7.5 | 25 |
| 3 | 70 | 15 | 15 | 50 |
| 4 | 70 | 7.5 | 22.5 | 75 |
| 5 | 70 | 3 | 27 | 90 |

Then each of the equilibrium liquids in liquid phase was contacted with the zeolite adsorbent as obtained above, and from the change in the compositions of the equilibrium liquid before and after the contact with the zeolite adsorbent was obtained the adsorptive selectivity of the desorbent for p-xylene. The results are shown in Table 2.

TABLE 2

| Run No. | Desorbent (weight %) Desorbent | Selectivity of Desorbent over p-Xylene Desorbent/p-Xylene + | | | | |
|---|---|---|---|---|---|---|
|  |  | 10 | 25 | 50 | 75 | 90 |
| 1 | Diisopropyl ether | 0.98 | 0.95 | 0.95 | 0.94 | 0.91 |
| 2 | Diisobutyl ether | 0.67 | 0.65 | 0.64 | 0.60 | 0.54 |
| 3 | Di-sec-butyl ether | 0.41 | 0.38 | 0.35 | 0.34 | 0.34 |
| 4 | Di-tert-butyl ether | 0.72 | 0.65 | 0.57 | 0.48 | 0.31 |
| 5 | Di-n-amyl ether | 0.60 | 0.56 | 0.48 | 0.43 | 0.33 |
| 6 | Diisoamyl ether | 0.42 | 0.38 | 0.36 | 0.33 | 0.31 |
| 7 | Di-tert-amyl ether | 0.48 | 0.42 | 0.38 | 0.32 | 0.31 |
| 8 | Furan | 2.9 | 2.6 | 2.3 | 2.2 | 1.5 |
| 9 | 2-Methylfuran | 1.8 | 1.3 | 1.0 | 0.89 | 0.75 |
| 10 | Hexamethylene oxide | 2.7 | 2.5 | 2.0 | 1.5 | 1.3 |
| 11 | 1,8-Cineole | 0.85 | 0.79 | 0.75 | 0.74 | 0.74 |
| Comparative Run No. |  |  |  |  |  |  |
| 1 | Anisole | 9.0 | 7.5 | 7.2 | 6.7 | 5.1 |
| 2 | n-Hexyl ether | 0.52 | 0.41 | 0.33 | 0.28 | 0.21 |
| 3 | n-Butylbenzene | 0.38 | 0.33 | 0.25 | 0.21 | 0.19 |

EXAMPLE 1

A chromatographic separation apparatus was prepared by connecting 3 stainless steel chromatographic columns, each having an inner diameter of 8 mm and a length of 2,000 mm, equipped with a jacket and a distributor for dispersing liquid at the top of the column and a collector for distributing liquid at the bottom of the column with one another through 3 stainless steel pipe having an inner diameter of 1 mm. Each column was uniformly packed with the zeolite adsorbent having a particle size of 60 to 100 mesh (about 150 to 250 microns) as obtained in Referential Example 1.

Then the columns packed with the zeolite was maintained at 120° C. and first, a desorbent as set forth in Table 3 was supplied to the columns to condition the zeolite adsorbent and secondly, 50 ml of an $C_8$ isomer mixture containing 15% of p-xylene, 20% of ethylbenzene, 45% of m-xylene and 20% of o-xylene were supplied to the columns by a metering pump for minute quantity to form an $C_8$ isomer mixture adsorption zone. Then the desorbent was fed to the column again at a constant flow rate of 9.5 cc/minute to develop the $C_8$ isomer mixture adsorption band and the effluent flowed from the bottom of the column was divided into fractions of about 1 to about 10 cc and collected. The weight percents of the p-xylene, ethylbenzene, m-xylene, o-xylene and desorbent in a sample liquid thus collected were quantitatively analyzed by gas chromatography. A liquid rich in other $C_8$ isomers than p-xylene was obtained from the frontal boundary portion of the $C_8$ isomer mixture adsorption band in the flow direction of the effluent and a liquid rich in p-xylene was obtained from the rear boundary portion.

As the criteria for the efficiency of separation, the weight of p-xylene in a fraction where the purity of p-xylene was at least 99% as compared with the purity of other $C_8$ isomers [$S_{99}$ (g)]; the concentration of p-xylene in its entire fraction [$C_{99}$ (weight %)]; and the average concentration of the $C_8$ isomer mixture in the adsorption band at the outlet for collection [Total $C_8$ (weight %)] were measured. The results are shown in Table 3.

TABLE 3

| Run No. | Desorbent | $S_{99}$ (g) | $C_{99}$ (%) | Total $C_8$ (%) |
|---|---|---|---|---|
| 1 | Diisopropyl ether | 1.61 | 11.2 | 49.1 |
| 2 | Furan | 1.53 | 10.8 | 50.2 |
| 3 | Hexamethylene oxide | 1.54 | 10.3 | 48.6 |
| Comparative Run No. | | | | |
| 1 | Anisole | 0.33 | 6.1 | 36.5 |
| 2 | n-Butylbenzene | 1.01 | 5.3 | 38.6 | pump for minute quantity to form a $C_8$ isomer mixture adsorption band. Then the desorbent was fed to the columns again at a constant flow rate of 7.5 cc/minute to develop the $C_8$ isomer mixture adsorption band. The effluent flowed from the bottom of the columns was divided into fractions of 1 to 10 cc and collected. The sample liquids thus collected were quantitatively analyzed by gas chromatography in the same manner as in Example 1. In the flow direction of the effluent, a liquid rich in m-xylene was obtained from the frontal boundary portion of the $C_8$ isomer mixture adsorption band and a liquid rich in ethylbenzene was obtained from the rear boundary portion.

As the criteria for the efficiency of separation, the weight of m-xylene in a fraction where the purity of m-xylene was 99% as compared to ethylbenzene [S m-xylene (g)]; the concentration of m-xylene in its entire fraction [C m-xylene (weight %]; the weight of ethylbenzene in a fraction where the purity of ethylbenzene was at least 99% as compared with p-xylene [S ethylbenzene (g)]; the concentration of ethylbenzene in its entire fraction [C ethylbenzene (weight %)]; and the average concentration of the $C_8$ isomer mixture adsorption band at the outlet for collection [Total $C_8$ (weight %)] were measured. The results are shown in Table 5.

TABLE 5

| Run No. | Desorbent | S m-xylene (g) | C m-xylene (%) | S ethylbenzene (g) | C ethylbenzene (%) | Total $C_8$ (%) |
|---|---|---|---|---|---|---|
| 1 | Diisopropyl ether | 8.31 | 26.2 | 8.18 | 28.4 | 53.4 |
| 2 | 1,8-Cineole | 7.94 | 27.1 | 8.20 | 29.1 | 54.1 |
| 3 | Diisobutyl ether | 8.41 | 25.9 | 7.74 | 27.4 | 51.2 |
| Comparative Run No. | | | | | | |
| 1 | n-Hexyl ether | 5.11 | 10.7 | 4.08 | 7.6 | 40.1 |
| 2 | n-Butylbenzene | 4.76 | 13.6 | 4.66 | 9.7 | 37.8 |

COMPARATIVE EXAMPLE 1

In the same manner as in Referential Example 1, 55% of the ion exchangeable sites located on a commercially available synthetic faujasite structured zeolite type Y (Na type; mole ratio of $SiO_2/Al_2O_3=4.8$) were replaced by potassium ion. Then the zeolite thus ion-exchanged was thoroughly washed with water and calcined at 400° C. for 2 hours. The zeolite adsorbent thus prepared was packed in the same chromatographic separation apparatus as in Example 1 and a chromatographic separation was conducted using a desorbent as set forth in Table 4 in the same manner and under the same conditions as in Example 1. The results are shown in Table 4.

TABLE 4

| Run No. | Desorbent | $S_{99}$ (g) | $C_{99}$ (%) | Total $C_8$ (%) |
|---|---|---|---|---|
| 1 | Diisopropyl ether | 0.11 | 3.2 | 46.3 |
| 2 | Furan | 0.13 | 3.1 | 47.2 |

EXAMPLE 2

Using the same chromatographic separation apparatus and the same zeolite adsorbent as in Example 1, the columns packed with the zeolite adsorbent were maintained at 120° C. and firstly, a desorbent as set forth in Table 5 was supplied to the columns to condition the zeolite adsorbent and secondly, 50 ml of an $C_8$ isomer mixture containing 50% of ethylbenzene and 50% of m-xylene were supplied to the columns by a metering

What is claimed is:

1. A process for the adsorption separation of $C_8$ aromatic isomers which comprises the steps of:
   (a) Supplying a $C_8$ aromatic isomer mixture to a separation zone packed with a zeolite adsorbent to form an $C_8$ aromatic isomer mixture adsorption band, the zeolite being a faujasite structured zeolite where at least about 60% of the exchangeable cation sites are replaced by potassium ion, and the remaining exchangeable cation sites being replaced by at least one metal cation selected from the group consisting of sodium, lithium, rubidium, cesium, magnesium, calcium, strontium, barium, nickel, copper, silver, manganese, cadmium, thallium and lanthanum ions;
   (b) Supplying a desorbent to the separation zone to develop the $C_8$ aromatic isomer mixture adsorption band, the desorbent being an ether compound having a substantially constant selectivity, within the range of about 0.3 to about 3.0, over para-xylene measured at a concentration of about 10 to about 90% by weight of the ether compound in the mixture of the ether compound and para-xylene;
   (c) Repeating the step (a) and the step (b) alternately to effect the migration of the $C_8$ isomer mixture adsorption band; and
   (d) Collecting the entire amount of the $C_8$ aromatic isomer in fractions at the outlet of the separation zone.

2. The process of claim 1, wherein the zeolite which has been subjected to a calcination at a temperature ranging from about 100° C. to a temperature below the decomposition of the faujasite structure for about 3 to about 72 hours is used.

3. The process of claim 1, wherein the faujasite structured zeolite where at least about 60% of the exchangeable cation sites are replaced by potassium ion and the remaining exchangeable cation sites are replaced with at least one cation selected from the group consisting of lithium, barium, thallium and cesium ions is used.

4. The process of claim 1, wherein a synthetic zeolite of type Y is used as the faujasite structured zeolite.

5. The process of claim 1, wherein the ether compound is selected from the group consisting of diisopropyl ether, diisobutyl ether, di-sec-butyl ether, di-tert-butyl ether, di-n-amyl ether, diisoamyl ether, di-tert-amyl ether, furan, 2-methylfuran, hexamethylene oxide, 1,4-cineole and 1,8-cineole.

6. The process of claim 1, wherein the desorbent is an ether compound having a selectivity of about 0.5 to about 1.5 over para-xylene measured at a concentration of about 10 to about 90% by weight of the ether compound in the mixture of the ether compound and the para-xylene.

7. The process of claim 6, wherein the ether compound is diisopropyl ether.

8. The process of claim 6, wherein the ether compound is diisobutyl ether.

9. The process of claim 6, wherein the ether compound is 1,8-cineole.

10. The process of claim 1, wherein the faujasite structure zeolite has a $SiO_2$ to $Al_2O_3$ mole ratio of at least about 4.0.

11. The process of claim 1, wherein the $C_8$ aromatic isomer mixture contains ethylbenzene or para-xylene and at least one isomer selected from the group consisting of meta-xylene, ortho-xylene, ethylbenzene and p-xylene.

12. The process of claim 11, wherein the $C_8$ aromatic isomer mixture contains meta-xylene, ortho-xylene, ethylbenzene and para-xylene.

13. A process for the separation of $C_8$ aromatic isomers of claim 1 which comprises the steps of:
(a) Supplying a $C_8$ aromatic isomer mixture containing at least one of ortho-xylene and meta-xylene, and in addition, ethylbenzene and para-xylene to a first separation zone packed with a zeolite adsorbent to form a $C_8$ aromatic isomer mixture adsorption band;
(b) Supplying a desorbent to the separation zone to develop the $C_8$ aromatic isomer mixture adsorption band where the following regions (A), (B), (C), (D) and (E) in the order to the direction of migration are formed,
Region (A) containing ortho-xylene and/or meta-xylene,
Region (B) containing ortho-xylene and/or meta-xylene and ethylbenzene,
Region (C) containing a ortho-xylene and/or meta-xylene, ethylbenzene and para-xylene, the region (C) being missing if the regions (A) and (B) contain the total amount of ortho-xylene and meta-xylene and the regions (D) and (E) contain the total amount of para-xylene,
Region (D) containing ethylbenzene and para-xylene, and
Region (E) containing para-xylene;
(c) Repeating the step (a) and the step (b) alternately to effect the migration of the $C_8$ aromatic isomer mixture adsorption band; and
(d) Collecting the entire amount of the regions (A), (B), (C), (D) and (E) in fractions at the outlet of the separation zone.

14. The process of claim 13, wherein the process includes collecting para-xylene as a product from region (E).

15. The process of claim 13, wherein the process includes supplying the $C_8$ aromatic isomer mixture collected from region (D) to a second separation zone packed with a zeolite adsorbent to form a $C_8$ aromatic isomer mixture adsorption band, supplying a desorbent to the second separation zone to develop the $C_8$ aromatic isomer mixture adsorption band, repeating the above described two steps alternately to effect the migration of the $C_8$ aromatic isomer mixture adsorption band and collecting ethylbenzene and para-xylene as a product, respectively.

16. The process of claim 13, wherein the process includes recycling the $C_8$ aromatic isomer mixture collected from region (C) to the first separation zone for re-use.

17. The process of claim 13, wherein the process includes passing at least part of the ortho-xylene and/or meta-xylene collected from region (A) to an isomerization zone to convert at least part of the ortho-xylene and/or meta-xylene to ethylbenzene and/or para-xylene and recycling an isomerization effluent containing the ethylbenzene and/or para-xylene converted to the first separation zone for re-use.

18. The process of claim 13, wherein the process includes supplying the $C_8$ aromatic isomer mixture collected from region (B) to a third separation zone packed with a zeolite adsorbent to form a $C_8$ aromatic isomer mixture adsorption band, supplying a desorbent to the third separation zone to develop the $C_8$ aromatic isomer mixture adsorption band, repeating the above described two steps alternately to effect the migration of the $C_8$ aromatic isomer mixture adsorption band, collecting ethylbenzene as a product and combining ortho-xylene and/or meta-xylene with the $C_8$ aromatic isomer mixture collected from region (A) together.

19. The process of claim 13, wherein the process includes passing the $C_8$ isomer mixture collected from region (B) together with the ortho-xylene and/or meta-xylene collected from region (A) to an isomerization zone.

20. The process of claim 13, wherein the process includes separating the desorbent from a mixture of the desorbent and any of the $C_8$ aromatic isomers collected from the first separation zone by distillation before passing the $C_8$ aromatic isomer mixture to an isomerization zone or another separation zone or before collecting the $C_8$ aromatic isomer as a product.

21. The process of claim 15 or 18, wherein the same desorbent is employed in the first, second and third separation zones.

22. The process of claim 15 or 18, wherein the zeolite packed in the first, second and third separation zones is a faujasite structured zeolite having a $SiO_2$ to $Al_2O_3$ mole ratio of at least about 4.0.

* * * * *